(12) United States Patent
Nejikovsky et al.

(10) Patent No.: US 6,995,556 B2
(45) Date of Patent: Feb. 7, 2006

(54) ELECTROMAGNETIC GAGE SENSING SYSTEM AND METHOD FOR RAILROAD TRACK INSPECTION

(75) Inventors: Boris Nejikovsky, Springfield, VA (US); Gary A. Carr, Fairfax, VA (US)

(73) Assignee: ENSCO, Inc., Falls Church, VA (US)

(*) Notice: Subject to any disclaimer, the term of this patent is extended or adjusted under 35 U.S.C. 154(b) by 179 days.

(21) Appl. No.: 10/622,773

(22) Filed: Jul. 21, 2003

(65) Prior Publication Data

US 2004/0095135 A1 May 20, 2004

Related U.S. Application Data

(60) Provisional application No. 60/397,662, filed on Jul. 23, 2002.

(51) Int. Cl.
*B61K 9/10* (2006.01)
*G01N 27/82* (2006.01)

(52) U.S. Cl. .................... 324/217; 324/207.17; 33/338

(58) Field of Classification Search ................ 324/222, 324/217, 207.17, 207.22, 207.15, 207.2, 324/207.21, 207.24, 207.26; 33/338, 287, 33/1 Q, 523.1, 651.1
See application file for complete search history.

(56) References Cited

U.S. PATENT DOCUMENTS

| 2,311,715 A | * | 2/1943 | Thorne ..................... 324/217 |
|---|---|---|---|
| 3,505,742 A | * | 4/1970 | Fiechter .................... 33/338 |
| 3,515,984 A | * | 6/1970 | McClaren et al. .......... 324/217 |
| 3,864,039 A | * | 2/1975 | Wilmarth ................... 356/625 |
| 3,990,154 A | * | 11/1976 | Theurer et al. ............ 33/523.2 |
| 4,144,519 A | | 3/1979 | Chamuel |
| 4,160,204 A | | 7/1979 | Holmgren et al. |
| 4,181,430 A | * | 1/1980 | Shirota et al. ............. 365/3.06 |
| 4,259,018 A | * | 3/1981 | Poirier ....................... 356/625 |
| 4,417,208 A | | 11/1983 | Hachtel et al. |
| 4,704,577 A | | 11/1987 | Junker et al. |
| 4,866,380 A | | 9/1989 | Meins et al. |
| 4,904,939 A | | 2/1990 | Mian |
| 5,094,004 A | * | 3/1992 | Wooten ...................... 33/338 |
| 5,554,933 A | * | 9/1996 | Logue ........................ 324/233 |
| 5,636,026 A | | 6/1997 | Mian et al. |
| 5,949,293 A | | 9/1999 | Akamatsu et al. |
| 6,397,130 B1 | * | 5/2002 | Carr et al. ................... 701/19 |
| 2003/0140509 A1 | * | 7/2003 | Casagrande ................. 33/287 |

FOREIGN PATENT DOCUMENTS

| JP | 54-50358 | | 4/1979 |
|---|---|---|---|
| JP | 55-52901 | | 4/1980 |
| JP | 357173701 A | * | 10/1982 |
| JP | 358082103 A | * | 5/1983 |

* cited by examiner

*Primary Examiner*—Bot Ledynh
*Assistant Examiner*—Kenneth J. Whittington
(74) *Attorney, Agent, or Firm*—Nixon Peabody LLP; Jeffrey L. Costellia

(57) ABSTRACT

An electromagnetic gage sensing system having sensor heads positioned over each rail of a railroad track that measures both rail gage and height distance above the rails of a railroad track. Each sensor head includes an array of electromagnetic field generating coils and an array of electromagnetic field sensors positioned above each rail so as to extend substantially across the rail surface. A method of measuring gage distance is also provided in which lateral EM field output signal indicative of an edge surface of a rail is sensed.

57 Claims, 3 Drawing Sheets

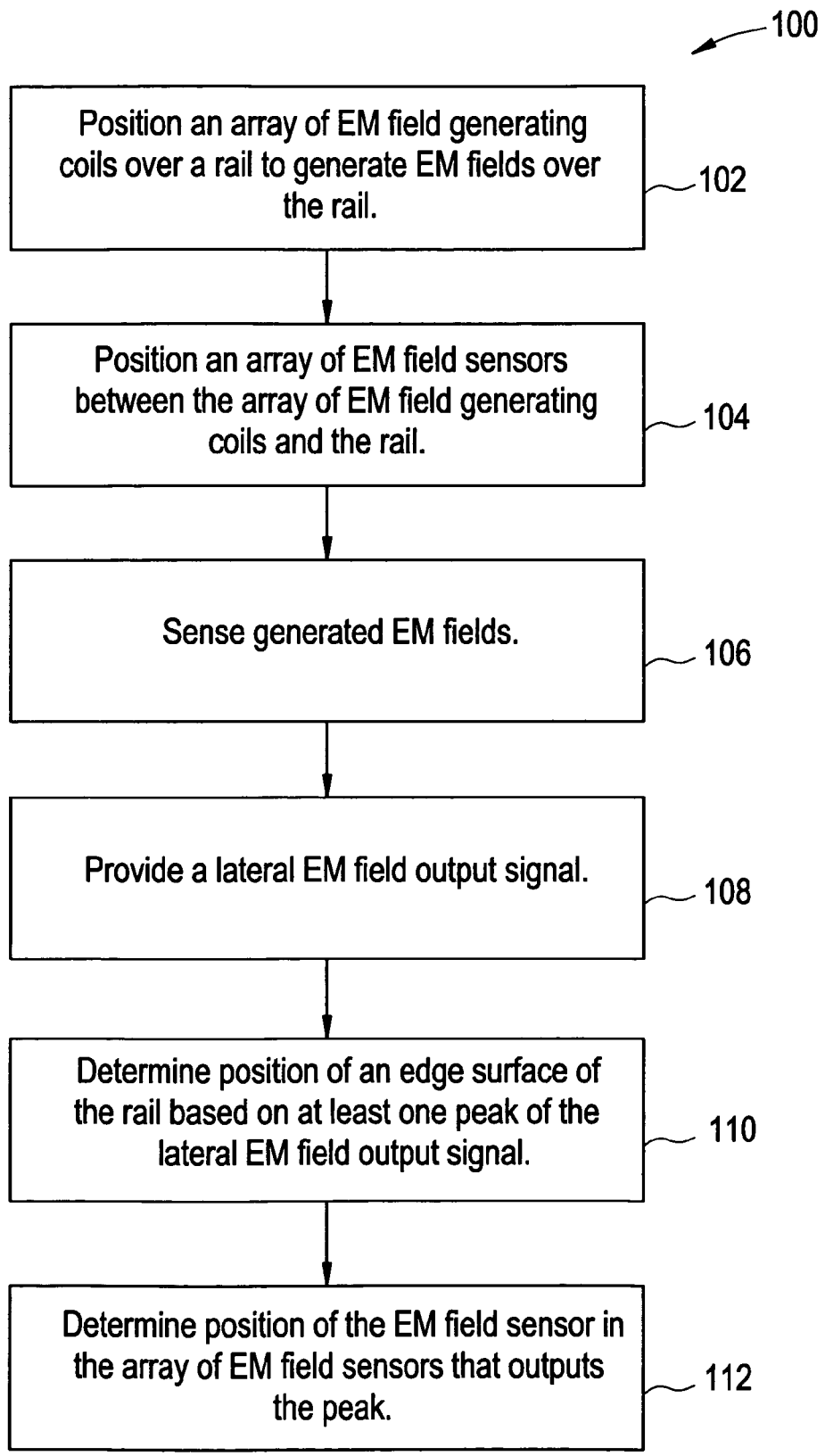

ELECTROMAGNETIC GAGE SENSING SYSTEM AND METHOD FOR RAILROAD TRACK INSPECTION

This application claims priority to U.S. Provisional Application No. 60/397,662, filed Jul. 23, 2002.

BACKGROUND OF THE INVENTION

1. Field of the Invention

The present invention is generally directed to gage sensing systems and methods for inspecting railroad tracks. More specifically, the present invention is directed to an electromagnetic gage sensing system and method.

2. Description of the Related Art

Gage sensors and sensing systems currently used by various U.S. railroads to measure and inspect gage distance between rails of a railroad track are generally based on optical, mechanical contact, or electromagnetic measurement technologies.

The optical gage sensing systems and methods that use optical technologies provide high level of accuracy but have inherent weather and reliability limitations. Such optical gage sensing systems are readily effected by rain, snow, dirt, and other environmental conditions. In addition, such optical gage sensing systems require periodic cleaning of lenses or protective windows to remove dirt, grease, oil, and other substances typically present in the railroad environment. Such optical gage sensing systems are also known to become saturated and provide inaccurate readings when sunlight reflected by the shiny rail surface reflects directly into the sensing system.

The performance and accuracy of mechanical contact gage sensing systems and methods are not as sensitive to weather conditions as optical gage measurement sensing systems. However, such contact gage sensing systems are not sufficiently reliable or accurate. In particular, contact gage sensing systems often become damaged by switches and other objects near the railroad track, thereby decreasing the accuracy and reliability of the resultant measurement. Contact gage sensing systems also require frequent maintenance due to the normal wear and tear of contact wheels or other contacting components that are typically used in such systems.

An electromagnetic gage sensing system and method of measurement has been developed that utilize a single proximity sensor to determine the distance to the gage surface of the rail. An electro-mechanical tracking system is used in conjunction therewith to continuously adjust the proximity sensor's position to maintain a fixed distance between the proximity sensor and the rail of the railroad track. The proximity sensor is located below the top of the rail and near the rail gage surface. However, the electromagnetic gage sensor, as described is not reliable because the sensor is easily damaged by switches, grade crossings, and other obstructions that may be present along the railroad track. Correspondingly, the electromechanical tracking system requires periodic servicing and maintenance which increases costs associated with operating such a system.

Japanese Patent 55-52901 issued to Shirota et al. discloses a non-contact measurement of gage between the rails of a railroad track by detecting the change in impedance due to magnetic induction, such as eddy current. A pair of detectors are positioned directly over the contact surface of the rails to allow determination of the rail position. In addition, another pair of detectors are angled toward the inner surface of the rails to allow determination of the gage distance between the rails of the railroad track. The pairs of detectors are mounted on a mounting base so that they are fixed at a predetermined position. The gage distance between the rails of the railroad track is calculated in accordance with an equation disclosed in the reference.

The main disadvantage of the solution proposed in Japanese Patent 55-52901 is that high level of accuracy of gage measurements cannot be achieved due to the significant lateral motion of the rail of up to 60–70 mm, relative to the sensor mounting location. This lateral motion is caused by continuous changes in position of the rail vehicle bogie where the detectors are mounted, relative to the rails of the railroad track. The width of the rail head of the railroad track is typically 50 mm. To obtain accurate data, the height above the rail should be measured at the center of the rail head while the gage should be measured slightly below the top of the rail. However, due to the significant motion of the detectors relative to the rail, the detectors point to wrong locations on the rails of the railroad track so that the obtained measurements are inaccurate.

The above noted disadvantage and limitation of the system disclosed in Japanese Patent 55-52901 is compounded by the fact that the proposed solution of this reference is also sensitive to rail metal composition. In particular, the detectors used in the disclosed system operate based on the magnitude of the magnetic induction measurements. However, magnitude of the magnetic induction measurements vary depending on the material of the rail, i.e. the metal composition of the rail. When an inspection car moves along the railroad track, the material properties of the rails of the railroad track will change, based on various parameters such as oldrail versus new rail, different types of rail, rust and so on. All of these variations cause changes in the magnitude of the output thereby limiting the accuracy of the measurements obtained utilizing such a system.

Therefore, there still exists an unfulfilled need for a system and method for a non-contact electromagnetic gage measuring system. There also exists a need for such a system and method that provides reliable and accurate gage and/or height measurements for rails of the railroad track. In addition, there further exists an unfulfilled need for such an electromagnetic gage sensing system and method that is resistant to environmental conditions and rail metal composition.

SUMMARY OF THE INVENTION

In view of the foregoing, an advantage of the present invention is in providing a non-contact electromagnetic gage sensing system and method thereof that provides reliable and accurate gage and/or height measurements for rails of the railroad track.

Another advantage of the present invention is in providing such an electromagnetic gage sensing system and method that is resistant to environmental conditions and rail metal composition.

Yet another advantage of the present invention is in providing such an electromagnetic gage sensing system and method in which electromagnetic fields allows measurement of both lateral and vertical distances.

These and other advantages are provided by an electromagnetic (EM) gage sensing system for measuring at least gage distance between rails of a railroad track in accordance with the various embodiments of the present invention. In one embodiment, the EM gage sensing system comprises a first array of EM field generating coils extending substantially across the first rail and beyond an edge surface of the first rail, the first array of EM field generating coils being adapted to generate an EM field, a first array of EM field sensors positioned substantially between the first rail and the first array of EM field generating coils, the first array of EM field sensors being adapted to sense the EM field generated by the first array of EM field generating coils, and provide a first lateral EM field output signal, and a processor adapted to process the first lateral EM field output signal to determine position of the edge surface of the first rail.

In accordance with one embodiment of the present invention, the position of the edge surface of the first rail is determined by the processor based on at least one peak of the first lateral EM field output signal. In this regard, the position of the edge surface of the first rail is determined by the processor based on position of an EM field sensor of the first array of EM field sensors that outputs the peak of the first lateral EM field output signal. The processor may be further adapted to calculate a first gage based on position of the EM field sensor of the first array of EM field sensors that outputs the peak. Moreover, the processor may further be adapted to average the first lateral EM field output signal over a predetermined length of travel along the first rail.

In accordance with another embodiment, the first array of EM field sensors may be further adapted to provide a first vertical EM field output signal indicative of height distance of the first rail. In this regard, the processor may be further adapted to process the first vertical EM field output signal to determine height distance of the first rail based on magnitude of a valley of the first vertical EM field output signal. Moreover, the processor may further be adapted to average the first vertical EM field output signal over a predetermined length of travel along the first rail.

In accordance with still another embodiment, the EM gage sensing system may further comprise a second sensor positioned over a second rail of the railroad track, the second sensor extending substantially across the second rail and beyond an edge surface of the second rail, the second sensor including a second array of EM field generating coils adapted to generate an EM field, and a second array of EM field sensors adapted to sense the EM field generated by the second array of EM field generating coils, and to provide a second lateral EM field output signal indicative of position of the edge surface of the second rail.

In the above embodiment, the position of the edge surface of the second rail may be determined by the processor based on at least one peak of the second lateral EM field output signal. In this regard, the position of the edge surface of the second rail may be determined by the processor based on the position of an EM field sensor of the second array of EM field sensors that outputs the peak of the second lateral EM field output signal. The processor may further be adapted to calculate a second gage based on the position of the EM field sensor of the second array of EM field sensors that outputs the peak. The processor may further be adapted to calculate a total gage by adding the first gage, the second gage and a distance between the first array of EM field sensors and the second array of EM field sensors.

In addition, the second array of EM field sensors may further be adapted to provide a second vertical EM field output signal indicative of height distance of the second rail. In this regard, the processor may further be adapted to process the second vertical EM field output signal to determine height distance of the second rail based on magnitudes of a valley of the second vertical EM field output signal. The processor may be further adapted to average the second lateral EM field output signal and/or the second vertical EM field output signal over a predetermined length of travel along the second rail.

In yet another embodiment of the present invention, the EM gage sensing system may further include a fixture. The fixture may be adapted to mount the first array of EM field generating coils and the first array of EM field sensors over the first rail, and/or the second array of EM field generating coils and the second array of EM field sensors over the second rail.

In still another embodiment of the present invention, the processor of the EM gage sensing system may be implemented as a neural network based processor which is adapted to receive the lateral and vertical EM field output signals from the array of EM field sensors, and to calculate gage and height distance above the rail.

In accordance with another aspect of the present invention, a method of measuring gage distance between rails of a railroad track is provided, the method comprising the steps of positioning an array of electromagnetic (EM) field generating coils over a rail of the railroad track to generate EM fields over the rail, positioning an array of EM field sensors substantially between the EM field generating coils and the rail, sensing EM fields, and providing at least a lateral EM field output signal indicative of position of an edge surface of the rail.

In accordance with one embodiment, the method further includes the step of determining the position of an edge surface of the rail based on at least one peak of the lateral EM field output signal. In this regard, the step of determining the position of the edge surface includes the step of determining the position of an EM field sensor in the array of EM field sensors that outputs the at least one peak. The method may also include the step of averaging the lateral EM field output signal over a predetermined length of travel along the rail.

The method may further include the step of providing a vertical EM field output signal indicative of height distance of the rail. In this regard, the method may further include the step of determining height distance of the rail based on at least one valley of the vertical EM field output signal. The method may also include the step of averaging the vertical EM field output signal over a predetermined length of travel along the rail.

In accordance with still another aspect of the present invention, a method of measuring at least gage distance between rails of a railroad track is provided comprising the steps of positioning a first array of electromagnetic (EM) field generating coils over a first rail of the railroad track, positioning a first array of EM field sensors substantially between the first array of EM field generating coils and the first rail, each EM field sensor of the first array of EM field sensors sensing the EM field generated over the first rail and providing a corresponding output, determining which EM field sensor of the first array of EM field sensors is providing strongest output, and determining the position of an edge surface of the first rail based on the position of the EM field sensor of the first array of EM field sensors providing strongest output.

In accordance with another embodiment, the method may further include the step of calculating a first gage based on position of the EM field sensor of the first array of EM field sensors providing the strongest output. The method may also include the step of averaging the outputs of the EM field sensors of the first array of EM field sensors over a predetermined length of travel along the first rail.

In accordance with still another embodiment, the method may also include the step of determining a first height distance between the first rail and the first array of EM field sensors based on a vertical component of the outputs of the EM field sensors of the first array of EM field sensors. This may be obtained by determining a minimum of the outputs of the EM field sensors of the first array of EM field sensors.

In accordance with another embodiment of the present invention, the method may also comprise the steps of positioning a second array of electromagnetic (EM) field generating coils over a second rail of the railroad track, positioning a second array of EM field sensors substantially between the second array of EM field generating coils and the second rail, each EM field sensor of the second array of EM field sensors sensing EM fields generated over the second rail and providing a corresponding output, determining which EM field sensor of the second array of EM field sensors is providing strongest output, and determining the position of the edge surface of the second rail based on the position of the EM field sensor of the second array of EM field sensors providing the strongest output.

In accordance with one embodiment, the method may further include the step of calculating a second gage based on the position of the EM field sensor of the second array of EM field sensors providing the strongest output. In this regard, the method may further include the step of calculating a total gage between the first rail and the second rail by adding the first gage, the second gage, and a distance between the first array of EM field sensors and the second array of EM field sensors.

The method may further include the step of averaging the outputs of the EM field sensors of the second array of EM field sensors over a predetermined length of travel along the second rail. In addition, the method may further include the step of determining a second height distance between the second rail and the second array of EM field sensors based on a vertical component of the outputs of the EM field sensors of the second array of EM field sensors. In this regard, the step of determining the second height distance may include the step of determining a minimum of the outputs of the EM field sensors of the second array of EM field sensors.

The method may further include the step of processing the EM field output signal using a processor. In this regard, the processor may be a neural network based processor. The method may further include the step of training the neural network based processor using a data set. The data set may include various rail types and range of locations of the rail relative to the EM field sensor arrays.

These and other advantages and features of the present invention will become more apparent from the following detailed description of the preferred embodiments of the present invention when viewed in conjunction with the accompanying drawings.

BRIEF DESCRIPTION OF THE DRAWINGS

FIG. 5 shows a flow diagram illustrating a method for measuring gage distance between rails of a railroad track in accordance with another aspect of the present invention.

DETAILED DESCRIPTION OF THE PREFERRED EMBODIMENT

Figure 1:
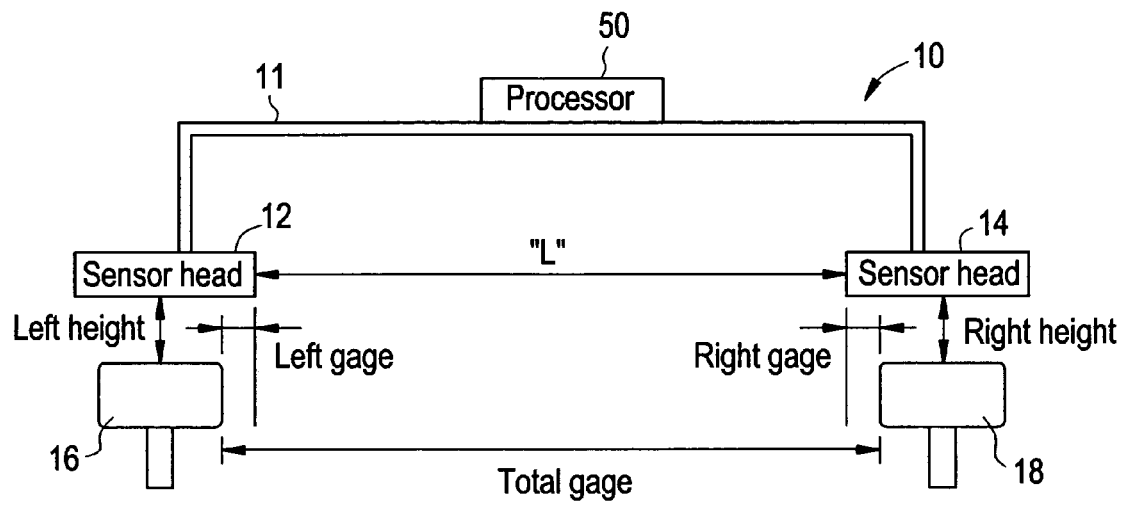
FIG. 1 is a schematic illustration of an electromagnetic gage sensing system in accordance with one embodiment of the present invention.

FIG. 1 is a schematic illustration of an electromagnetic gage sensing system 10 in accordance with one embodiment of the present invention. As will be evident from the discussion herein below, the electromagnetic gage sensing system 10 is a non-contact system that provides reliable and accurate gage and height measurement for the rails of the railroad track. In addition, the electromagnetic gage sensing system 10 is resistant to environmental conditions and rail metal composition thereby providing improved accuracy and performance as compared to prior art gage sensing systems.

The electromagnetic gage sensing system 10 of the illustrated embodiment of FIG. 1 includes a left sensor head 12, a right sensor head 14, and a processor 50, the details of which are discussed in further detail below. The left sensor head 12 and the right sensor head 14 are mounted to a fixture 11 so that distance "L" between the left sensor head 12 and the sensor 14 is known. Preferably, the distance L between the sensors is fixed.

It should initially be noted that fixture 11 may be a separate structure for the purpose of mounting the sensor heads 12 and 14, or the fixture 11 may alternatively be any component of the train such as a railroad car body or a truck so that the sensor heads 12 and 14 are mounted directly to the railroad car body or the truck. In addition, it should also be noted that left and right designations are used herein merely to clarify which sensor and which rail is being referred to in the various figures. In this regard, the left sensor head 12 and the right sensor head 14 may be substantially the same in construction and operation. Furthermore, whereas specific dimensions of the sensors sensor heads, their dimensions, and their positioning relative to the rails of the railroad track are recited below, it should be understood that such specific dimensions are provided for illustrative purposes only and other embodiments may be implemented differently.

In accordance with the illustrated embodiment of the sensing system 10, the left sensor head 12 and the right sensor head 14 are adapted to measure lateral and vertical components of an electromagnetic (EM) field. Due to installation variances wear, etc., the gage and/or height distance measurements for any particular portion of the railroad track will vary along the track. The sensing system 10 may be used in the manner described in further detail below to determine the gage and/or height distance to allow accurate inspection of the railroad track regardless of such variances.

In the illustrated embodiment, the left sensor head 12 and the right sensor head 14 are mounted by the fixture 11, for example, at approximately 1.5 inches above the surface of the left rail 16 and the right rail 18, respectively. The left sensor head 12 measures the lateral position of the edge of the left rail 16 to determine the left gage, while the right sensor head 14 measures the lateral position of the right rail 18 to determine the right gage as shown in FIG. 1. Using the left gage and the right gage in conjunction with the known distance L between the left sensor head 12 and the right sensor head 14, the total gage measurement for the railroad track may then be calculated as follows:

Total Gage=(Left gage)+L+(Right gage)

In addition to gage measurements, the left sensor head 12 measures the left height distance between the left sensor head 12 and top of the left rail 16, while the right sensor head 14 measures the right height distance between the right sensor head 14 and top of the right rail 18 as also shown in FIG. 1. The height information maybe used to correct left and right gage measurements, to calculate cross level (i.e. elevation of one rail above another rail), and/or other track geometries or parameters.

Figure 2:
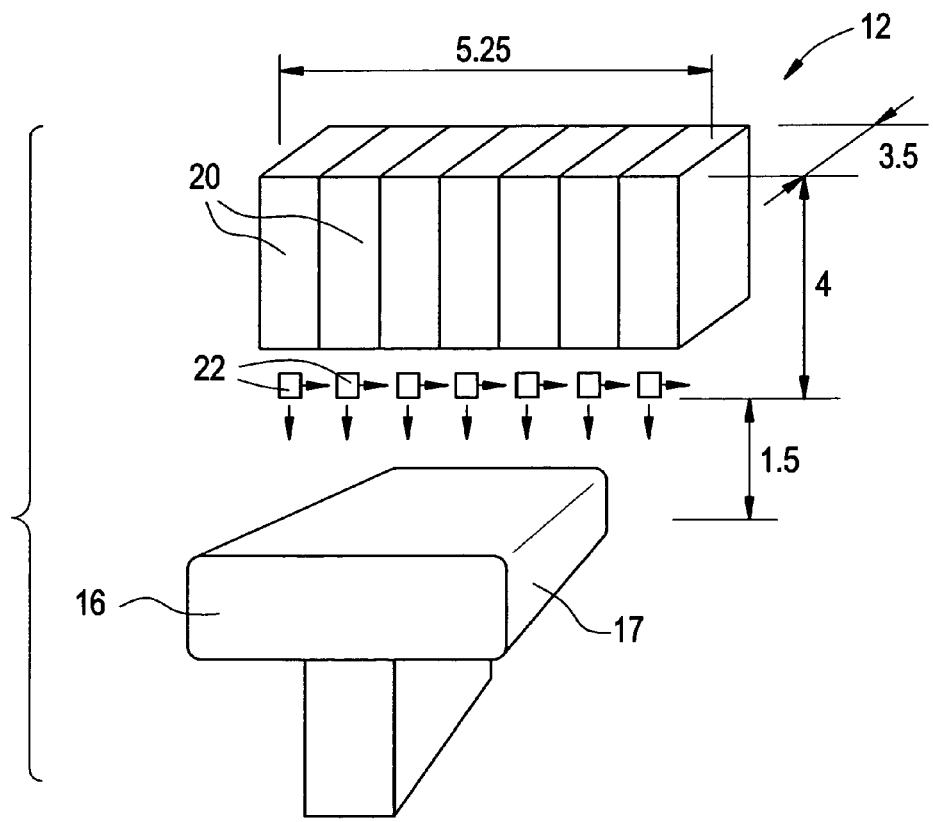
FIG. 2 is an enlarged schematic view of the internal components of one sensor head and one rail of the railroad track.

The details of the left sensor head 12 are schematically illustrated in FIG. 2, the various internal components housed in the left sensor head 12 so that the function of the components of the left sensor head 12 can be more readily described. As previously noted, the left sensor head 12 and the right sensor head 14 are substantially similar in accordance with the preferred embodiment of the present invention. Thus, the right sensor head 14 would have a substantially similar configuration as the left sensor shown in FIG. 2. However, discussion of the right sensor head 14 is omitted herein to avoid repetition.

As shown, the left sensor bead 12 includes an array of electromagnetic (EM) field generating coils 20, seven being shown in the illustrated embodiment of FIG. 2. The left sensor head 12 also includes an array of two axis (lateral and vertical) EM field strength sensors 22 correspondingly positioned between the left rail 16 and the generating coils 20, the field strength sensors 22 being adapted to detect EM field strength from each of the generating coils 20. As shown, the array of generating coils 20 and the array of field strength sensors 22 are positioned above the left rail 16 so that they extend across the left rail 16 over a substantial area of the left rail 16. In this regard, in the illustrated example, the generating coils 20 and the strength sensors 22 extend beyond edge surface 17 of the left rail 16 toward the area between the left rail 16 and the right rail 18 so that they are positioned where the edge surface 17 of the left rail 16 may be positioned as the rail car moves along the left rail 16.

The generating coils 20 are powered by alternating current at a frequency preferably between 1 KHz and 9 KHz. Of course, alternating current at frequencies below 1 KHz may also be used. However, resolution may be diminished and such an embodiment may also be sensitive to imperfections in the rail being measured. Thus, frequencies above 1 KHz are preferred. Each EM field sensor 22 is centered under a corresponding generating coil 20 and is adapted to measure the EM field produced by the generating coils 20. Such measurement of the EM field may be continuous or may be intermittent. In the presence of the left rail 16, the array of field sensors 22 measure the EM field that is generated by the array of generating coils 20 which is altered by the left rail 16 in the manner further described in detail below. In the absence of the left rail 16, the array of field sensors 22 measure undisturbed EM field produced by the array of generating coils 20. Therefore, in absence of the left rail 16, the lateral component of the EM field as sensed by the array of field sensors 22 is approximately zero.

Referring again to FIG. 2, the generating coils 20 are rectangular in the illustrated embodiment to increase sensitivity and measurement resolution. The width of the generating coils 20, i.e. dimension of each generating coil across the rail of the railroad track, should be small enough to be able to provide accurate resolution regarding the position of the edge surface 17 of the left rail 16. Therefore, the width of the generating coils 20 is preferably substantially less than the width of the left rail 16. In order to provide increased signal strength at the left rail 16, the length of the generating coils 20, i.e. dimension of each generating coil along the rail of the railroad track, is preferably more than two times larger than the height dimension above the rail. Thus, in the illustrated embodiment of FIG. 2, the generating coils 20 have a length that is at least twice that of the left height. Of course, the above described configuration is merely one example and in other embodiments, the generating coils 20 may have a different shape and may be dimensioned with different proportions than as shown.

In the illustrated embodiment of FIG. 2, the left sensor head 12 is provided with seven generating coils 20 which are adjacently stacked together to provide an array of generating coils which is approximately 5.25 inches in width, and 3.5 inches in length. As can be seen the width of the generating coils 20 is substantially less than the width of the left rail 16. In addition, the length of the generating coils 20 is 3.5 inches which is more than two times the left height of 1.5 inch above the left rail 16. As previously note, this allows increased sensitivity and measurement resolution. The right sensor head 14 would also have a similar configuration so that the generating coils and the strength sensors of the right sensor head 14 extend beyond edge surface of the right rail 18 toward the area between the left rail 16 and the right rail 18. Of course, the above described embodiment of the left sensor head 12, and correspondingly, the right sensor head 14, is merely one example and the present invention is not limited to this example. In this regard, different number of generating coils may be provided with different dimensions than that described above.

As explained in further detail below, when the left rail 16 is positioned under the left sensor head 12, both vertical and lateral field components of the EM field generated by the array of generating coils 20 change. This change to the EM field is mostly due to the eddy currents induced by the generating coils 20 in the surface of the left rail 16. Of course, the vertical and lateral field components of the EM field generated by the array of generating coils of the right sensor head 14 would likewise be changed when the right rail 18 is positioned under the right sensor head 14.

Figure 3:
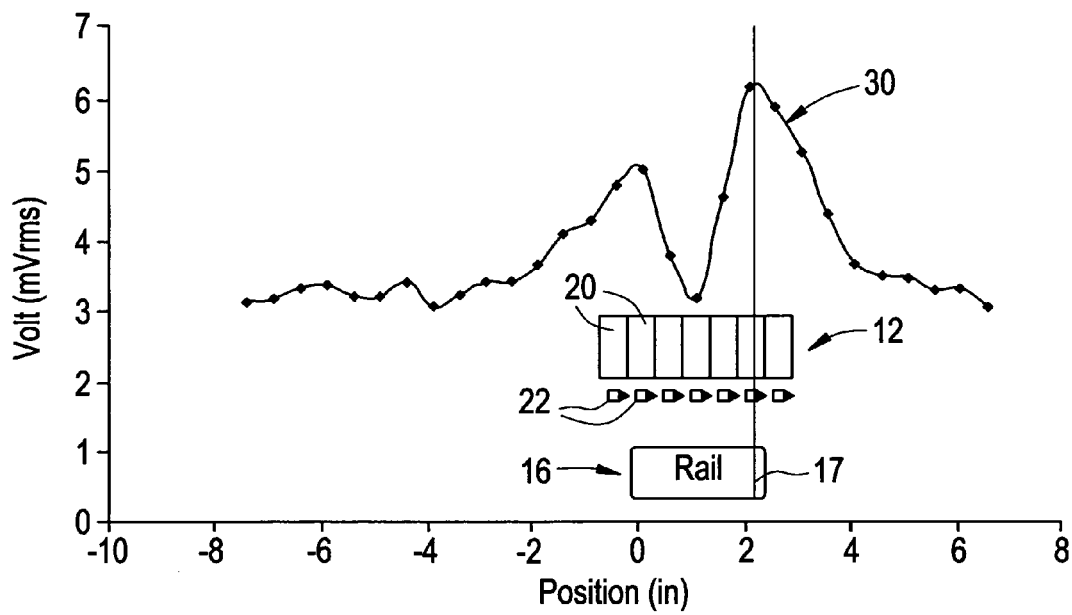
FIG. 3 is a graph showing an example lateral electromagnetic field output of the sensor of FIG. 2 in response to the position of the rail.

FIG. 3 shows the lateral EM field output signal 30 of the left sensor head 12 in response to the position of the left rail 16. The lateral EM field output signal 30 is generated from the lateral components of the output signals from each of the field sensors 22 that measure the lateral EM field of each of the generating coils 20. As shown, the peaks of the lateral EM field output signal 30, as measured by the array of EM field sensors 22 of the left sensor head 12, occurs at the location of the left sensor head 12 that is directly above the edge surface 17 of the left rail 16 and the outer edge surface on the other side of the left rail 16.

Thus, as evident from examination of the lateral EM field output signal 30 as shown in FIG. 3, the lateral component of the output signal from the left sensor head 12 is highly sensitive to the location of the edge surface 17 of the left rail. In the illustrated embodiment, the lateral component of the EM field is the strongest near the edge surface 17 from which gage is measured. Consequently, because the position of each of the field sensors 22 of the left sensor head 12 is known, the position of the field sensor 22 that is positioned above the edge surface 17 and provides the highest peak of the lateral EM field output signal 30 may be used to accurately determine the position of the edge surface 17 relative to the left sensor head 12. Therefore, the known position of the field sensor 22 that provides the highest peak of the lateral EM field output signal 30 may be used to provide accurate left gage measurement as shown in FIG. 1.

Figure 4:
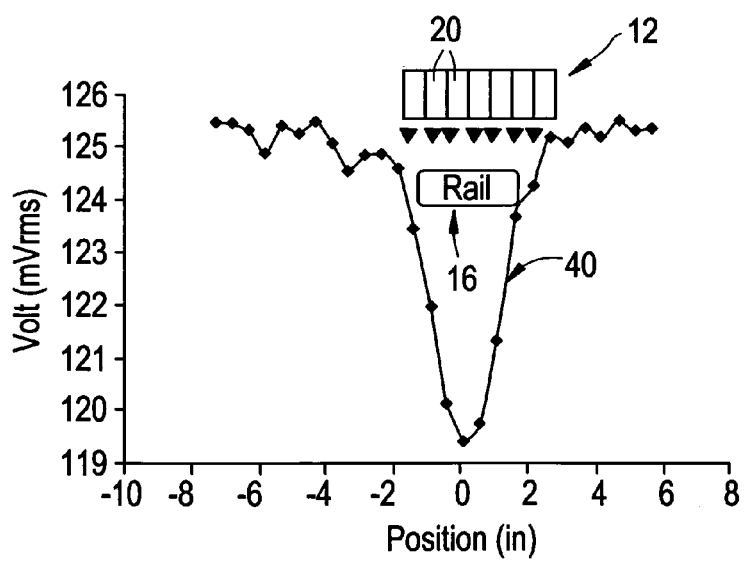
FIG. 4 is a graph showing an example vertical electromagnetic field output of the sensor of FIG. 2 in response to the position of the rail.

FIG. 4 shows the vertical EM field output signal 40 of the left sensor head 12 in response to the position of the left rail 16. The vertical EM field output signal 40 is generated from the vertical components of the output signals from each of the field sensors 22. As shown by the valley of the vertical EM field output signal 40, the vertical EM field component as measured by the left sensor head 12, achieves its minimum at substantially the center of the left rail 16. The actual value of the vertical EM field component, i.e. the magnitude of the valley in the vertical EM field output signal 40, is dependent on the distance between the left sensor head 12 and the left rail 16. Therefore, the vertical component of the output, signal of the left sensor head 12 may be used to determine the left height distance between the left sensor head 12 and the left rail 16.

The processor 50 of the electromagnetic gage sensing system 10 monitors the lateral output signals from each of the EM field sensors 22 of the left sensor head 12 to determine the position of the edge surface 17 of the left rail 16 which is identified as left gage in the illustration of FIG. 1. In particular, the processor 50 determines where the peaks occur in the lateral EM field output signal 30 to determine the location of the edge surface 17 of the left rail 16 relative to the left sensor head 12. Of course, as shown in FIG. 3, the lateral EM field output signal 30 has two peaks, each corresponding to the edge surfaces of the left rail 16. However, the processor 50 is adapted to determine that the peak generated by the EM field sensor that is positioned toward the inner portion of the railroad track corresponds to the edge surface 17. Thus, whereas the second peak generated by the left sensor head 12 is determined to correspond to the edge surface 17 for determining the left gage, the first peak generated by the right sensor head 14 would correspond to the edge surface for determining the night gage.

Likewise, in the illustrated embodiment, the processor 50 also monitors the vertical output signals from the array of the EM field sensors 22 to determine the left height, i.e. the distance between the left sensor head 12 and the left rail 16. This is attained by the processor 50 which determines the magnitude of the valley in the vertical EM field output signal 40 which is correlated to an actual left height distance.

As previously noted, the right sensor head 14 would operate in a substantially similar manner as the left sensor head 12 discussed in detail above. Thus, the output signals from the right sensor head 14 are analyzed by the processor 50 in a similar manner to the output signals from the left sensor head 12. In particular, by measuring the lateral and vertical EM field output signals from the right sensor head 14, the right gage and right height distance as shown in FIG. 1 can be readily determined.

Thus, as explained above, the dimensions and position of the left sensor head 12, the right sensor head 14, and the EM field sensors housed therein, are all known parameters. Once the position of the edge surfaces of the left rail 16 and the right rail 18 are determined, the left gage and the right gage as shown in FIG. 1 can be readily determined. In addition, as previously described, the left sensor head 12 and the right sensor head 14 are mounted to a fixture 11 so that distance "L" between the left sensor head 12 and the right sensor head 14 is also known. Therefore, by adding distance L together with the left gage and the right gage, the total gage between the left rail 16 and the right rail 18 can be determined using the electromagnetic gage sensing system 10 of the illustrated embodiment. Moreover, because the electromagnetic gage sensing system 10 of the present embodiment also monitors the left height and the right height show in FIG. 1, any discrepancy between the height position of the rails can also be determined.

A significant advantage of the electromagnetic gage sensing system 10 in accordance with the present invention is that unlike other gage sensing systems, changes in composition of rail material, ambient temperature, AC voltage applied to the generating coils, and other common factors do not significantly affect the accuracy of the electromagnetic gage sensing system 10. This accuracy is attained by the fact that processor 50 looks for a location of a peak lateral EM field component in the lateral EM field output signal 40, and not its absolute value. Of course, the above-mentioned factors may affect accuracy of the height measurement since the height dimensions are derived by determining the absolute value of the valley in the vertical EM field component of the vertical EM field output signal.

Preferably, in order to make measurements less sensitive to cracks and other small deviations in the surfaces of left rail 16, the left sensor head 12 are adapted to generate and sense EM fields with relatively low frequency, for instance, between 1 KHz and 9 KHz. This low frequency EM field generated by the generating coils 20 creates eddy currents with relatively deep penetration into the metal surface of the left rail 16. Therefore, surface cracks have less detriment to providing accurate measurements.

In addition, the processor 50 in accordance with one embodiment may be further adapted to average the EM field measurements over a predetermined length of travel along the left rail 16, for instance, 1 foot along the left rail 16. This averaging of the EM field measurements over a length of travel along the left track 16 further decreases the influence of small, local field deviations caused by cracks and other small imperfections in the surfaces of left rail 16. The right sensor head 14 may, of course, be operated in a substantially similar manner at relatively low frequencies to decrease influence of small, local field deviations in the surfaces of the right rail 18.

In accordance with one embodiment, the processor 50 of the EM gage sensing system 10 may be implemented as a neural network based processor which is adapted to receive the lateral and vertical EM field output signals from the array of EM field sensors of the left sensor head 12 and/or the right sensor head 14, and to calculate gage and height distance above the rail in the manner previous described. Of course, the processor 50 may be implemented in any appropriate manner and neural network based processor is merely one example. However, the neural network based processor implementation of the processor 50 provides certain advantages over conventional processors. In particular, if implemented as a neural network based processor, the processor 50 can be trained to provide enhanced accuracy. Training of the processor 50 may be accomplished using several different rail types and the training data set made to cover the entire expected range of rail positions relative to the array of EM field sensors of the left and/or right sensor heads so that the training data set is representative of real life operating scenarios of the EM gage sensing system 10. This allows the processor 50 to learn the relationship between the EM field output from the array of field sensors, and the actual physical parameters corresponding thereto, such as the actual gage and height distance above the rail.

FIG. 5 shows a flow diagram 100 illustrating a method for measuring gage distance between rails of a railroad track in accordance with another aspect of the present invention. As shown, the method of the illustrated embodiment includes step 102 in which an array of electromagnetic (EM) field generating coils are positioned over a rail of the railroad track to generate EM fields over the rail. In step 104, an, array of EM field sensors are positioned substantially between the array of EM field generating coils and the rail. The generated EM fields are sensed in step 106, and a lateral EM field output signal is provided in step 108, the lateral EM field output signal being indicative of the position of an edge surface of the rail.

The method for measuring gage distance shown in the flow diagram 100 also includes step 110 in which the position of an edge surface of the rail is determined based on at least one peak of the lateral EM field output signal provided in step 108. In this regard, the method is further provided with step 112 in which the position of an EM field sensor in the array of EM field sensors that outputs the peak is determined. Of course, the position of an edge surface of the adjacent rail of the railroad track may be determined in a similar manner as described above so that together with the distance between the array of EM sensors, the total gage distance of the railroad track can be determined.

Optionally, the above described method shown in flow diagram 100 may further include the step of providing a vertical EM field output signal indicative of height distance of the rail so that the height distance of the rail may be determined based on a valley of the vertical EM field output signal. The method may also optionally include the step of averaging the lateral EM field output signal and/or the vertical EM field output signal over a predetermined length of travel along the rail. Furthermore, if a neural network based processor is used in practicing the described method, an optional step of training the processor may also be provided, for example, using a training data set made to cover the entire expected range of rail positions in the manner previously described with several different rail types.

Thus, as described above, the electromagnetic gage sensing system in accordance with the present invention includes sensor heads having an array of EM field generating coils and an array EM field sensors that may be used to accurately detect the location of the rail edge surface thereby providing a reliable gage sensor that does not have the disadvantages of optical based gage measurement systems. In addition, the electromagnetic gage sensing system of the present embodiment also does not require moving or wearable parts so that limitations and disadvantages of such moving or wearable parts can be avoided. The use of eddy currents allows the electromagnetic gage sensing system to accurately detect edge surface and calculate gate of the rail tracks under any weather conditions as well as allowing determination of the vertical height of the rails as previously described.

The processor of the electromagnetic gage sensing system processes (for example, parallel processes) output signals from the arrays of EM field sensors and analyzes distribution of the EM field across thee rail surface to determine the gage distance, rather than the absolute sensor reading. Thus, as compared to the sensing systems of the prior art, the measurements are less sensitive to rail steel chemical composition, ambient temperature, generating voltage, and other factors. Moreover, by averaging the signals over a predetermined length of the railroad track, the effects of cracks and other small deviations in rail surfaces may be minimized.

In addition, it should also be evident in view of the above that a novel method of measuring gage distance between rails of a railroad track is provided. It should further be evident that the method of the present invention avoids the limitations and disadvantages of prior art methods for measuring gage distance between rails of a railroad track.

While various embodiments in accordance with the present invention have been shown and described, it is understood that the invention is not limited thereto. The present invention may be changed, modified and further applied by those skilled in the art. Therefore, this invention is not limited to the detail shown and described previously, but also includes all such changes and modifications.

We claim:

1. An electromagnetic (EM) gage sensing system for measuring at least gage distance between rails of a railroad track comprising:
    a first array of EM field generating coils extending substantially across said first rail and beyond an edge surface of said first rail, said first array of EM field generating coils being adapted to generate an EM field;
    a first array of EM field sensors positioned substantially between said first rail and said first array of EM field generating coils, said first array of EM field sensors being adapted to sense said EM field generated by said first array of EM field generating coils, and provide a first lateral EM field output signal; and
    a processor adapted to process said first lateral EM field output signal to determine position of said edge surface of said first rail.

2. The EM gage sensing system of claim 1, wherein said processor is adapted to determine position of said edge surface of said first rail based on at least one peak of said first lateral EM field output signal.

3. The EM gage sensing system of claim 2, wherein said processor is adapted to determine position of said edge surface of said first rail based on position of an EM field sensor of said first array of EM field sensors that outputs said at least one peak of said first lateral EM field output signal.

4. The EM gage sensing system of claim 3, wherein said processor is further adapted to calculate a first gage based on position of said EM field sensor of said first array of EM field sensors that outputs said at least one peak.

5. The EM gage sensing system of claim 1, wherein said processor is further adapted to average said first lateral EM field output signal over a predetermined length of travel along said first rail.

6. The EM gage sensing system of claim 1, wherein said first array of EM field sensors are further adapted to provide a first vertical EM field output signal indicative of height distance of said first rail.

7. The EM gage sensing system of claim 6, wherein said processor is further adapted to process said first vertical EM field output signal to determine height distance of said first rail.

8. The EM gage sensing system of claim 7, wherein said processor is adapted to determine height distance of said first rail based on magnitude of a valley of said first vertical EM field output signal.

9. The EM gage sensing system of claim 6, wherein said processor is further adapted to average said first vertical EM field output signal over a predetermined length of travel along said first rail.

10. The EM gage sensing system of claim 1, further comprising a second sensor positioned over a second rail of said railroad track, said second sensor extending substantially across said second rail and beyond an edge surface of said second rail, said second sensor including a second array of EM field generating coils adapted to generate an EM field, and a second array of EM field sensors adapted to sense said EM field generated by said second array of EM field generating coils, and to provide a second lateral EM field output signal indicative of position of said edge surface of said second rail.

11. The EM gage sensing system of claim 10, wherein said processor is adapted to determine position of said edge surface of said second rail based on at least one peak of said second lateral EM field output signal.

12. The EM gage sensing system of claim 11, wherein said processor is adapted to determine position of said edge surface of said second rail based on position of an EM field sensor of said second array of EM field sensors that outputs said at least one peak of said second lateral EM field output signal.

13. The EM gage sensing system of claim 12, wherein said processor is further adapted to calculate a second gage based on position of said EM field sensor of said second array of EM field sensors that outputs said at least one peak.

14. The EM gage sensing system of claim 13, wherein said processor is adapted to determine position of said edge surface of said first rail based on position of an EM field sensor of said first array of EM field sensors that outputs said at least one peak of said first lateral EM field output signal, said processor being further adapted to calculate a first gage based on position of said EM field sensor of said first array of EM field sensors that outputs said at least one peak.

15. The EM gage sensing system of claim 14, wherein said processor is further adapted to calculate a total gage by adding said first gage, said second gage and a distance between said first array of EM field sensors and said second array of EM field sensors.

16. The EM gage sensing system of claim 10, wherein said processor is further adapted to average said second lateral EM field output signal over a predetermined length of travel along said second rail.

17. The EM gage sensing system of claim 10, wherein said second array of EM field sensors are further adapted to provide a second vertical EM field output signal indicative of height distance of said second rail.

18. The EM gage sensing system of claim 17, wherein said processor is further adapted to process said second vertical EM field output signal to determine height distance of said second rail.

19. The EM gage sensing system of claim 18, wherein said processor is adapted to determine height distance of said second rail based on magnitude of a valley of said second vertical EM field output signal.

20. The EM gage sensing system of claim 17, wherein said processor is further adapted to average said second vertical EM field output signal over a predetermined length of travel along said second rail.

21. The EM gage sensing system of claim 10, further including a fixture adapted to mount said first array of EM field generating coils and said first array of EM field sensors over said first rail, and said second array of EM field generating coils and said second array of EM field sensors over said second rail.

22. The EM gage sensing system of claim 1, wherein said processor is a neural network based processor.

23. The EM gage sensing system of claim 22, wherein said processor is adapted to be trained.

24. The EM gage sensing system of claim 23, wherein said processor is adapted to be trained using a training data set covering an expected range of rail positions relative to said first array of EM field sensors.

25. The EM gage sensing system of claim 1, further including a fixture adapted to mount said first array of EM field generating coils and said first array of EM field sensors over said first rail.

26. The EM gage sensing system of claim 10, wherein said first array of EM field generating coils and said second array of EM field generating coils generate EM fields between 1 KHz and 9 KHz.

27. The EM gage sensing system of claim 1, wherein said first array of EM field generating coils generates an EM field between 1 KHz and 9 KHz.

28. A method of measuring at least gage distance between rails of a railroad track comprising the steps of:
    positioning an array of electromagnetic (EM) field generating coils over a rail of said railroad track to generate EM fields over said rail;
    positioning an array of EM field sensors substantially between said EM field generating coils and said rail; and
    sensing EM fields and providing at least a lateral EM field output signal indicative of position of an edge surface of said rail.

29. The method of claim 28, wherein said EM field generated is between 1 KHz and 9 KHz.

30. The method of claim 28, wherein said array of EM field generating coils and said array of EM field sensors are positioned to extend substantially across said rail beyond said edge surface.

31. The method of claim 28, further including the step of determining position of an edge surface of said rail based on at least one peak of said lateral EM field output signal.

32. The method of claim 31, wherein said step of determining position of said edge surface includes the step of determining position of an EM field sensor in said array of EM field sensors that outputs said at least one peak.

33. The method of claim 28, further including the step of averaging said lateral EM field output signal over a predetermined length of travel along said rail.

34. The method of claim 28, further including the step of providing a vertical EM field output signal indicative of height distance of said rail.

35. The method of claim 34, further including the step of determining height distance of said rail based on at least one valley of said vertical EM field output signal.

36. The method of claim 35, further including the step of averaging said vertical EM field output signal over a predetermined length of travel along said rail.

37. The method of claim 28, further including the step of processing said lateral EM field output signal to determine position of an edge surface of said rail.

38. The method of claim 37, wherein said step of processing said lateral EM field output signal to determine position of an edge surface of said rail is attained using a processor.

39. The method of claim 38, wherein said processor is a neural network based processor.

40. The method of claim 39, further including the step of training said processor.

41. The method of claim 40, wherein said step of training said processor is attained using a training data set covering an expected range of rail positions relative to said first array of EM field sensors.

42. A method of measuring at least gage distance between rails of a railroad track comprising the steps of:
    positioning a first array of electromagnetic (EM) field generating coils over a first rail of said railroad track, said first array of EM field generating coils extending substantially across said first rail beyond an edge surface of said first rail to generate an EM field over said first rail;

positioning a first array of EM field sensors substantially between said first array of EM field generating coils and said first rail, said first array of EM field sensors extending substantially across said first rail beyond said edge surface of said first rail, each EM field sensor of said first array of EM field sensors sensing said EM field generated over said first rail and providing a corresponding output;

determining which EM field sensor of said first array of EM field sensors is providing strongest output; and determining position of said edge surface of said first rail based on position of said EM field sensor of said first array of EM field sensors providing strongest output.

43. The method of claim 42, further including the step of calculating a first gage based on position of said EM field sensor of said first array of EM field sensors providing strongest output.

44. The method of claim 42, further including the step of averaging said outputs of said EM field sensors of said first array of EM field sensors over a predetermined length of travel along said first rail.

45. The method of claim 42, further including the step of determining a first height distance between said first rail and said first array of EM field sensors based on a vertical component of said outputs of said EM field sensors of said first array of EM field sensors.

46. The method of claim 45, wherein said step of determining said first height distance includes the step of determining a minimum of said outputs of said EM field sensors of said first array of EM field sensors.

47. The method of claim 42, further comprising the steps of:

positioning a second array of electromagnetic (EM) field generating coils over a second rail of said railroad track, said second array of EM field generating coils extending substantially across said second rail beyond an edge surface of said second rail to generate an EM field over said second rail;

positioning a second array of EM field sensors substantially between said second array of EM field generating coils and said second rail, said second array of EM field sensors extending substantially across said second rail beyond said edge surface of said second rail, each EM field sensor of said second array of EM field sensors sensing EM fields generated over said second rail and providing a corresponding output;

determining which EM field sensor of said second array of EM field sensors is providing strongest output; and determining position of said edge surface of said second rail based on position of said EM field sensor of said second array of EM field sensors providing strongest output.

48. The method of claim 47, further including the step of calculating a second gage based on position of said EM field sensor of said second array of EM field sensors providing strongest output.

49. The method of claim 48, further including the step of calculating a first gage based on position of said EM field sensor of said first array of EM field sensors providing strongest output.

50. The method of claim 49, further including the step of calculating a total gage between said first rail and said second rail by adding said first gage, said second gage, and a distance between said first array of EM field sensors and said second array of EM field sensors.

51. The method of claim 47, further including the step of averaging said outputs of said EM field sensors of said second array of EM field sensors over a predetermined length of travel along said second rail.

52. The method of claim 47, further including the step of determining a second height distance between said second rail and said second array of EM field sensors based on a vertical component of said outputs of said EM field sensors of said second array of EM field sensors.

53. The method of claim 47, wherein said step of determining said second height distance includes the step of determining a minimum of said outputs of said EM field sensors of said second array of EM field sensors.

54. The method of claim 42, wherein said step of determining position of said edge surface of said first rail based on position of said EM field sensor of said first array of EM field sensors providing strongest output is attained using a processor.

55. The method of claim 54, wherein said processor is a neural network based processor.

56. The method of claim 55, further including the step of training said processor.

57. The method of claim 56, wherein said step of training said processor is attained using a training data set covering an expected range of rail positions relative to said first array of EM field sensors.

* * * * *